United States Patent
Lennartz et al.

(10) Patent No.: US 12,048,474 B2
(45) Date of Patent: Jul. 30, 2024

(54) SYSTEMS AND METHODS FOR PERFORMING A TISSUE SEAL

(71) Applicant: Covidien LP, Mansfield, MA (US)

(72) Inventors: Amanda H. Lennartz, Erie, CO (US); Kenlyn Bonn, Lakewood, CO (US); Tyler J. Bagrosky, Arvada, CO (US)

(73) Assignee: Covidien LP, Mansfield, MA (US)

( * ) Notice: Subject to any disclaimer, the term of this patent is extended or adjusted under 35 U.S.C. 154(b) by 442 days.

(21) Appl. No.: 16/953,449

(22) Filed: Nov. 20, 2020

(65) Prior Publication Data

US 2021/0153928 A1 May 27, 2021

Related U.S. Application Data

(60) Provisional application No. 62/938,514, filed on Nov. 21, 2019.

(51) Int. Cl.
*A61B 18/14* (2006.01)
*A61B 34/30* (2016.01)
*A61B 90/00* (2016.01)
*A61B 18/00* (2006.01)

(52) U.S. Cl.
CPC .......... *A61B 18/1445* (2013.01); *A61B 34/30* (2016.02); *A61B 90/37* (2016.02); *A61B 2018/00345* (2013.01); *A61B 2018/0063* (2013.01); *A61B 2018/00714* (2013.01)

(58) Field of Classification Search
CPC ..... A61B 18/1445; A61B 34/30; A61B 90/37; A61B 2018/00345; A61B 2018/0063; A61B 2018/00714; A61B 2018/00589; A61B 2018/00642; A61B 2018/00702; A61B 2018/00797; A61B 2018/00863; A61B 2018/00886; A61B 18/1233; A61B 2017/00026; A61B 34/25
See application file for complete search history.

(56) References Cited

U.S. PATENT DOCUMENTS

| | | | |
|---|---|---|---|
| 8,753,333 | B2 | 6/2014 | Johnson et al. |
| 9,123,155 | B2 | 9/2015 | Cunningham et al. |
| 9,592,095 | B2 | 3/2017 | Panescu et al. |
| 10,188,451 | B2 | 1/2019 | Peterson et al. |
| 10,607,345 | B2 | 3/2020 | Carnes et al. |
| 2007/0173811 | A1* | 7/2007 | Couture ............. A61B 18/1445 606/45 |
| 2011/0270121 | A1* | 11/2011 | Johnson ................. A61B 17/29 606/51 |
| 2012/0116267 | A1* | 5/2012 | Kimball ................. G16H 20/40 606/1 |
| 2012/0116365 | A1* | 5/2012 | Price ...................... A61B 90/40 606/1 |
| 2013/0345541 | A1* | 12/2013 | Nau, Jr. ................. A61B 18/24 600/407 |

(Continued)

*Primary Examiner* — Amanda K Hulbert
*Assistant Examiner* — Natasha Patel
(74) *Attorney, Agent, or Firm* — Carter, DeLuca & Farrell LLP

(57) ABSTRACT

A method of performing a tissue seal utilizing a robotic surgical system includes grasping tissue between a pair of jaws of an electrosurgical instrument; displaying on a display a visual representation of the grasped tissue; emitting electrosurgical energy from the pair of jaws into the tissue; and displaying on the display a visual representation of a progress of the tissue seal.

20 Claims, 3 Drawing Sheets

(56) References Cited

U.S. PATENT DOCUMENTS

| | | | |
|---|---|---|---|
| 2014/0025061 A1* | 1/2014 | Benamou | A61B 18/18 606/33 |
| 2015/0209035 A1* | 7/2015 | Zemlok | A61B 17/07207 73/1.01 |
| 2015/0223868 A1 | 8/2015 | Brandt et al. | |
| 2020/0197072 A1* | 6/2020 | Watson | A61B 90/37 |
| 2020/0222111 A1 | 7/2020 | Yates et al. | |

* cited by examiner

SYSTEMS AND METHODS FOR PERFORMING A TISSUE SEAL

CROSS-REFERENCE TO RELATED APPLICATION

This application claims the benefit of and priority to U.S. Provisional Application No. 62/938,514, filed on Nov. 21, 2019, the entire contents of which being incorporated by reference herein.

FIELD

The disclosure relates to robotics, and more specifically to methods of tissue sealing utilizing a robotic surgical system.

BACKGROUND

Open or endoscopic electrosurgical forceps utilize both mechanical clamping action and electrical energy to effect hemostasis. The electrode of each opposing jaw members is charged to a different electric potential such that when the jaw members grasp tissue, electrical energy can be selectively transferred through the tissue. A surgeon can either seal, cauterize, ablate, coagulate/desiccate, cut, dissect and/or simply reduce or slow bleeding, by controlling the intensity, frequency and duration of the electrosurgical energy applied between the electrodes and through the tissue. For the purposes herein, "coagulation" is defined as a process of desiccating tissue wherein the tissue cells are ruptured and dried. "Vessel sealing" is defined as the process of liquefying the collagen in the tissue so that it reforms into a fused mass with significantly-reduced demarcation between the opposing tissue structures (opposing walls of the lumen). Coagulation of small vessels is usually sufficient to permanently close them. Larger vessels need to be sealed to assure permanent closure.

To effectively seal tissue or vessels, especially thick tissue and large vessels, the following parameters must be accurately controlled: 1) the pressure applied to the vessel, which is ideally between about 3 kg/cm2 to about 16 kg/cm2; 2) the gap distance between the conductive tissue contacting surfaces (between about 0.001 and about 0.006 inches); and 3) the intensity, frequency, duration, and/or type of the electrosurgical energy.

SUMMARY

In accordance with an aspect of the present disclosure, a method of performing a tissue seal utilizing a robotic surgical system is provided and includes grasping tissue between a pair of jaws of an electrosurgical instrument coupled to a robotic surgical system; displaying on a display of the robotic surgical system a visual representation of the tissue; emitting electrosurgical energy from the pair of jaws into the grasped tissue, thereby changing a temperature of the grasped tissue; and displaying on the display a visual representation of the change of the temperature of the tissue as the electrosurgical energy is emitted from the pair of jaws into the grasped tissue.

In some aspects, the method may further include stopping emission of the electrosurgical energy after emitting the electrosurgical energy for a predetermined amount of time, and determining a status of the tissue.

In some aspects, the method may further include restarting emission of the electrosurgical energy into the tissue after the status of the tissue is determined.

In some aspects, the method may further include adjusting a level of the electrosurgical energy based on the determined status of the tissue.

In some aspects, the method may further include adjusting a grasping pressure applied to the tissue by the pair of jaws based on the determined status of the tissue.

In some aspects, the status of the tissue may be determined based on the temperature of the tissue and/or a perfusion of the tissue.

In some aspects, the status of the tissue may be determined based on a temperature of each of a plurality of sections of the tissue.

In some aspects, the predetermined amount of time corresponds to about a 5 percent completion of a seal of the tissue to about a 20 percent completion of the seal of the tissue.

In some aspects, the method may further include displaying on the display a visual representation of a progress of a seal of the tissue as the electrosurgical energy is emitted from the pair of jaws into the grasped tissue. The visual representation of the progress of the seal may include a number representing a percentage of a completed seal of the tissue.

In some aspects, the method may further include displaying on the display a visual representation of a level of electrosurgical energy being emitted by the pair of jaws into the grasped tissue.

In some aspects, the electrosurgical energy may include microwave energy, radiofrequency energy, bipolar energy, or ultrasonic energy.

In some aspects, the method may further include displaying on the display a temperature of the pair of jaws.

In some aspects, the method may further include determining a size of the grasped tissue, and displaying on the display a visual representation of the determined size of the grasped tissue.

In accordance with another aspect of the present disclosure, a method of performing a vessel seal utilizing a robotic surgical system is provided and includes grasping a vessel between a pair of jaws of an electrosurgical instrument coupled to a robotic surgical system; displaying on a display of the robotic surgical system a visual representation of the grasped vessel; emitting electrosurgical energy from the pair of jaws into the grasped vessel, thereby transitioning the vessel from an unsealed state toward a sealed state; and displaying on the display a visual representation of a progress of the transition of the vessel from the unsealed state toward the sealed state as the electrosurgical energy is emitted from the pair of jaws into the grasped tissue.

In some aspects, the visual representation of the progress of the seal may include a number representing a percentage of the seal of the vessel.

In some aspects, the visual representation of the progress of the vessel may include a change in a color of the displayed visual representation of the grasped vessel.

In some aspects, the method may further include stopping emission of the electrosurgical energy, and determining a status of the vessel.

In some aspects, the method may further include restarting emission of the electrosurgical energy into the vessel after the status of the vessel is determined.

In some aspects, the method may further include adjusting a level of the electrosurgical energy based on the determined status of the vessel.

In some aspects, the status of the vessel may be determined based on a temperature of the vessel or a perfusion of the vessel.

In some aspects, the emission of the electrosurgical energy may be stopped after determining that the seal of the vessel is at about 5 percent to about 20 percent of a complete seal.

Further details and aspects of various embodiments of the disclosure are described in more detail below with reference to the appended figures.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

BRIEF DESCRIPTION OF THE DRAWINGS

Embodiments of the disclosure are described herein with reference to the accompanying drawings, wherein.

Figure 1:
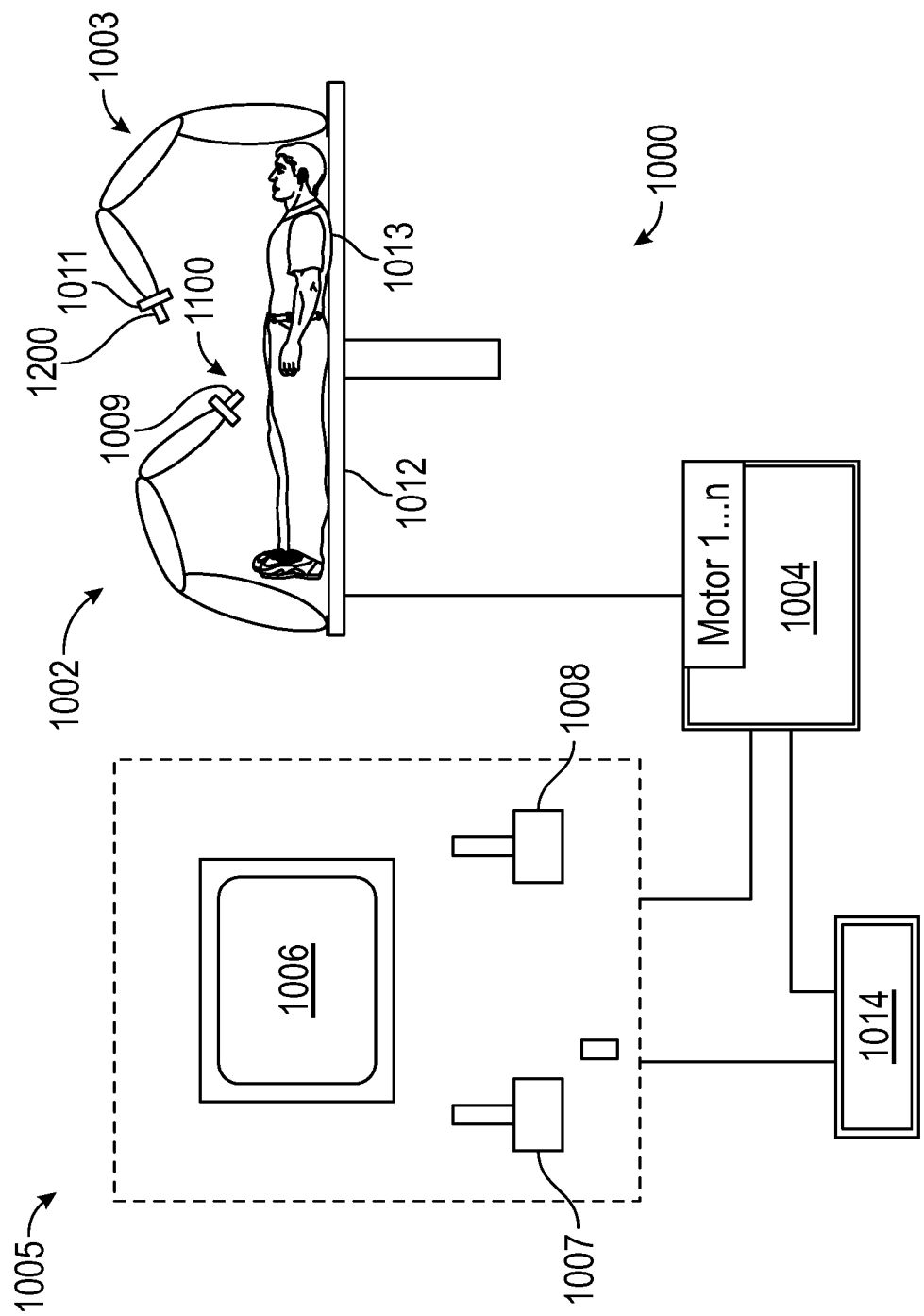
FIG. 1 is a schematic diagram of a robotic surgical system provided in accordance with aspects of the present disclosure.

Further details and aspects of exemplary embodiments of the disclosure are described in more detail below with reference to the appended figures. Any of the above aspects and embodiments of the disclosure may be combined without departing from the scope of the disclosure.

DETAILED DESCRIPTION

Embodiments of the presently disclosed devices, systems, and methods of treatment are described in detail with reference to the drawings, in which like reference numerals designate identical or corresponding elements in each of the several views. As used herein, the term "distal" refers to that portion of a structure that is farther from a user, while the term "proximal" refers to that portion of a structure that is closer to the user. The term "clinician" refers to a doctor, nurse, or other care provider and may include support personnel.

The present disclosure is generally directed to a method of sealing tissue, such as, for example, a vessel, an artery, a vein, or any other selected tissue type. The method may be carried out utilizing a robotic surgical system. During tissue sealing, the tissue is grasped between a pair of jaws of an electrosurgical instrument and energy (e.g., microwave energy, radiofrequency energy, bipolar energy, ultrasonic energy, etc.) is delivered from the electrosurgical instrument to the grasped tissue. The presently disclosed method visually displays the progress of the tissue seal throughout the tissue sealing procedure. In some aspects, the progress of the tissue seal may be represented visually by a virtual image of the vessel that changes color as the temperature of the tissue changes throughout the tissue sealing procedure. The method may further include an automatic ceasing of an application of grasping pressure and the application of energy at a time prior to completion of the tissue seal. Upon ceasing the application of energy, a plurality of tissue parameters may be measured to better assess the progress of the tissue seal. Some tissue parameters that may be measured include the temperature of the tissue throughout each section of the tissue, perfusion through the tissue, a size of a vessel, a color of the tissue, etc. Based on the measured tissue parameters, if it is determined that the grasped tissue is sealing properly, the application of energy may be continued. Alternatively, if it is determined that the grasped tissue is not sealing properly (e.g., the tissue is being desiccated), then the treatment may be adjusted by, for example, changing the amount of grasping pressure on the tissue and/or changing the intensity, frequency, or type of energy applied to the tissue.

With reference to FIG. 1, a robotic surgical system exemplifying the aspects and features of the present disclosure is shown identified by reference numeral 1000. Robotic surgical system 1000 includes a plurality of robot arms 1002, 1003; a control device 1004; and an operating console 1005 coupled with control device 1004. Operating console 1005 may include a display 1006, which may be set up in particular to display three-dimensional images; and manual input devices 1007, 1008, to enable a surgeon to telemanipulate robot arms 1002, 1003. Robotic surgical system 1000 may be configured for use on a patient 1013 lying on a patient table 1012 to be treated in a minimally invasive manner. Robotic surgical system 1000 may further include a database 1014 coupled to control device 1004, in which pre-operative data from patient 1013 and/or anatomical atlases are stored. Each of the robot arms 1002, 1003 may include a plurality of segments, which are connected through joints, and an attaching device 1009, 1011, to which may be attached, for example, an end effector assembly 1100, 1200, respectively.

Figure 2:
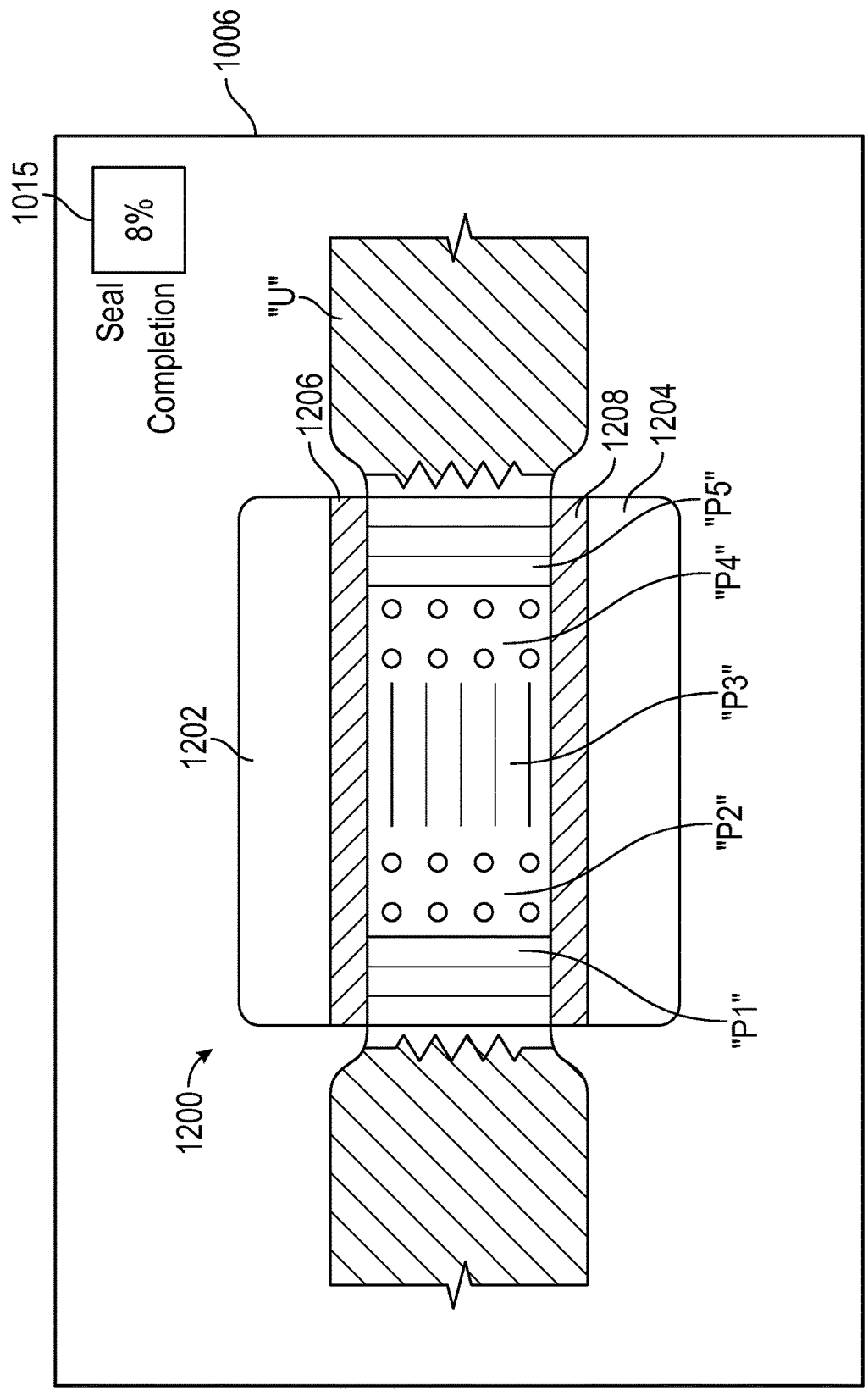
FIG. 2 is a plan view of a display of the robotic surgical system of FIG. 1 displaying a visual representation of a vessel grasped by and receiving energy from jaws of an end effector assembly.

With brief additional reference to FIG. 2, end effector assembly 1200 may include a pair of jaws 1202, 1204 configured to deliver treatment energy, such as microwave energy or radiofrequency energy. Each of the jaws 1202, 1204 has a conductive, tissue-sealing plate 1206, 1208 configured to be electrically coupled to a source of energy, such as, for example, a microwave energy source or a radiofrequency energy source. The plates 1206, 1208 are disposed in general vertical opposition relative to one another to facilitate grasping of tissue and tissue treatment. It is contemplated that that the robotic surgical system 1000 may include an electrosurgical instrument separate from the robot arm 1002, 1003 for manual control by a clinician. The electrosurgical instrument may be any one of a variety of instruments including bipolar instruments, monopolar instrument, ablation instruments, thermal treatment instruments, ultrasonic instruments, microwave instruments and radiofrequency instruments.

Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

The control device 1004 may include a processor (not shown) connected to a computer-readable storage medium or a memory, which may be a volatile type memory, such as RAM, or a non-volatile type memory, such as flash media, disk media, or other types of memory. In various embodiments, the processor may be another type of processor such as, without limitation, a digital signal processor, a microprocessor, an ASIC, a graphics processing unit (GPU), field-programmable gate array (FPGA), or a central processing unit (CPU). In various embodiments, the memory can be random access memory, read-only memory, magnetic disk memory, solid-state memory, optical disc memory, and/or another type of memory. The memory may communicate with the processor through communication buses of a circuit board and/or through communication cables such as serial ATA cables or other types of cables. The memory includes computer-readable instructions that are executable by the processor to operate the end effector assembly 1200.

Manual input devices 1007, 1008 of robotic surgical system 1000 may further include a motion activation control, a motion-sensing assembly including a motor, rotation and/or articulation lockout features, excessive torque limiting features, and/or a rotation control, similarly as detailed above, to provide the user with the ability to control manipulation of end effector assemblies 1100, 1200, by moving manual input devices 1007, 1008 relative to a reference position.

Figure 3:
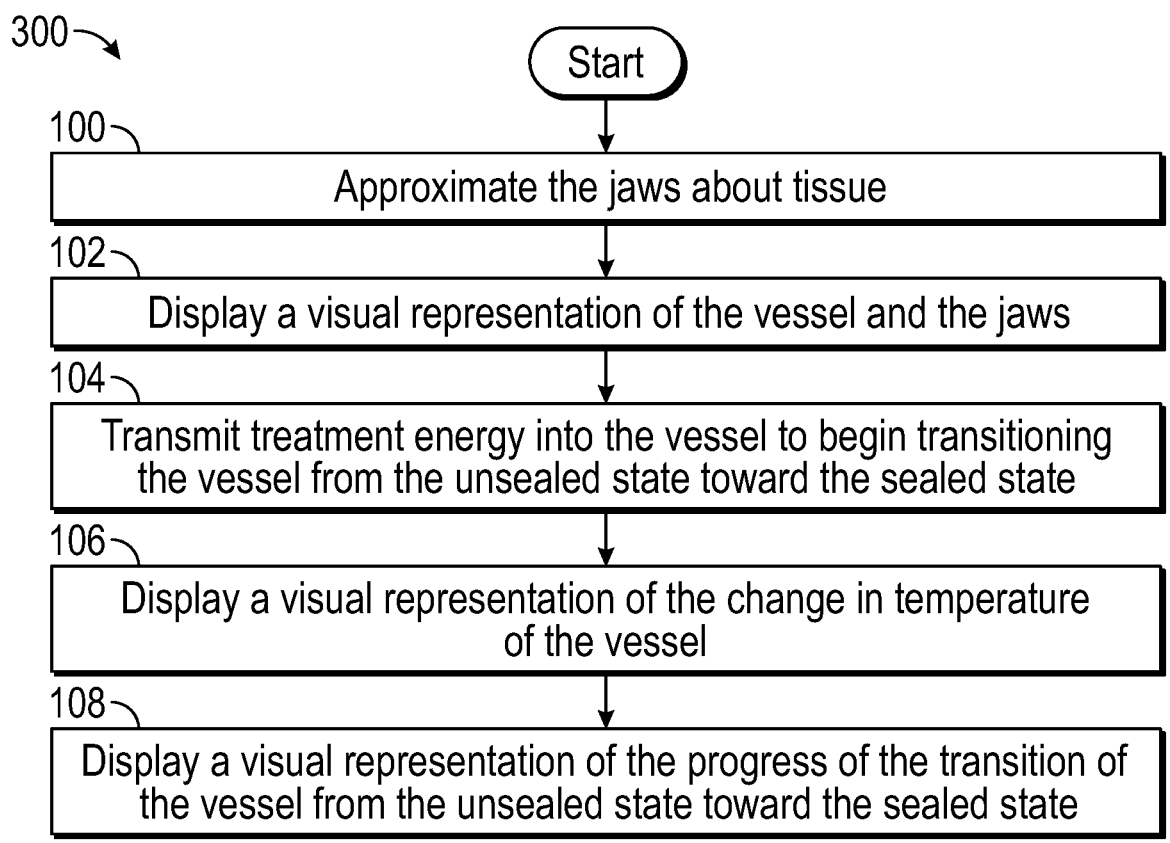
FIG. 3 is a flowchart illustrating an exemplary method for performing a tissue sealing procedure utilizing the robotic surgical system of FIG. 1.

With reference to FIGS. 2 and 3, a method of performing a tissue seal utilizing the robotic surgical system 1000 of FIG. 1 will now be described. It is contemplated that the methods of performing tissue seals described herein may alternatively be performed by a clinician without the assistance of the robotic surgical system 1000.

In step 100, the pair of jaws 1202, 1204 of the end effector assembly 1200 are approximated about tissue, such as, for example, a vessel "V," to apply an initial grasping pressure on the vessel "V." In step 102, the robotic surgical system 1000 displays on the display 1006 a visual representation of the vessel "V" grasped between the jaws 1202, 1204. While FIG. 2 illustrates a transverse cross-section of the jaws 1202, 1204 and the vessel "V," it is contemplated that the visual representation of the jaws 1202, 1204 and the vessel "V" may be other views, such as, perspective views, longitudinal cross-sections, or the like. In aspects, the thickness, type, and/or density of the vessel "V" may be determined and displayed on the display 1006 adjacent the displayed visual representation of the jaws 1202, 1204 and vessel "V."

In step 104, the robotic surgical system 1000 may automatically activate the electrosurgical energy source, such that the jaws 1202, 1204 transmit treatment energy (e.g., microwave energy or radiofrequency energy) into the vessel "V," thereby changing a temperature of the vessel "V" and transitioning the vessel "V" from an unsealed state toward a sealed state. In aspects, the clinician may be responsible for activating the electrosurgical energy source rather than the robotic surgical system 1000. As the treatment energy is transmitted, the display 1006 displays a visual representation of the level (e.g., intensity and frequency) of the treatment energy emitted by the jaws 1202, 1204. In aspects, the visual representation of the level of the treatment energy may be a number representing a percentage of the maximum amount of energy capable of being emitted by the jaws 1202, 1204.

In step 106, the control device 1004 of the robotic surgical system 1000 displays on the display 1006 a visual representation of the change of the temperature of the vessel "V." The change in temperature of the vessel "V" may be visually represented on the display 1006 by changing the color of the displayed vessel "V" based on a determined temperature of the vessel "V." As such, the end effector assembly 1200 may be equipped with temperature sensors (not shown) that determine the temperature of the vessel "V" along various portions "P1," "P2," "P3," "P4," "P5" of the vessel "V." The change in temperature of the vessel "V" may alternatively be visually represented on the display 1006 by changing a pattern, shading, or the like of each displayed portion "P1"-"P2" of the vessel "V." In this way, a clinician has a visual guide for determining a progress and/or degree of uniformity of the seal of the vessel "V" in real-time. In aspects, the temperature of the vessel "V," surrounding tissue, and/or the temperature of the jaws 1202, 1204 may be displayed on the display 1006 throughout the sealing process. If the temperature of the jaws 1202, 1204 are above, for example, about 40° C., the clinician may use this information to wait to grasp other tissue. Upon the jaws 1202, 1204 reaching a safe temperature for grasping sensitive tissues (e.g., nerves, bowel etc.), the display 1006 may be configured to flash or otherwise indicate that the jaws 1202, 1204 may be used to contact other tissue.

In step 108, the robotic surgical system 1000 may display on the display 1006 a visual representation of the progress of the vessel as it transitions from the unsealed state toward the sealed state. The visual representation of the progress of the seal may include a number representing a percentage of the completion of the seal of the vessel "V." The number may be provided in a sub-window 1015 (FIG. 2) on the display 1006. For example, if the robotic surgical system 1000 determines, based on information gathered from the sensors of the end effector assembly 1200, that the seal is at about 8% completion, the display 1006 displays in the sub-window 1015 "8%." In some aspects, the progress of the seal may be determined by viewing the change in color of the displayed visual representation of the vessel "V."

The robotic surgical system 1000 may be pre-programmed to automatically stop emission of the treatment energy from the jaws 1202, 1204 after a predetermined amount of time. The predetermined amount of time is the amount of time that it typically takes to accomplish about a 5 percent seal to about a 20 percent seal of a vessel of a similar type and thickness as the vessel "V," and the energy type and amount applied. In some aspects, the predetermined amount of time corresponds to about an 8 percent completion of the seal. The data, including the amount of time it takes to seal tissue of a particular type and thickness using energy of a particular type and amount, may be stored in the memory of the robotic surgical system 1000 and retrieved by the control device 1004 after determining the thickness and tissue type of the vessel "V" being operated on and the amount and type of energy selected for application. In some aspects, the robotic surgical system 1000 may be pre-programmed to automatically stop emission of the treatment energy after determining, based on, for example, impedance measurements, a 5 percent to about a 20 percent completion of the tissue seal.

After or upon stopping the emission of energy, a status of the vessel "V" (e.g., necrotic, ablated, sealed, cauterized, etc.) is determined by measuring a plurality of tissue parameters of the vessel "V." For example, using a plurality of suitable sensors arranged along the transverse axis of the plates 1206, 1208 of the end effector assembly 1200, the temperature of each of the portions "P1"-"P5" of the vessel "V" may be determined, a composition of the vessel "V" may be determined, a perfusion of the vessel "V" may be determined, or any other suitable tissue parameter may be determined to assist in assessing the overall status of the vessel "V."

After determining the status of the vessel "V," emission of the treatment energy into the vessel "V" may be restarted. If it is determined that the seal of the vessel "V" is progressing normally, the same amount of grasping pressure by the jaws 1202, 1204 may be applied and the same amount and type of treatment energy by may be applied. It is contemplated that the clinician may also determine the status of the tissue and the overall progress of the seal based on the displayed visual representation of the progress, and then determine whether any operative adjustments need to be made. As the robotic surgical system 1000 cycles between starting and stopping emission of the treatment energy, the robotic surgical system 1000 may prevent, using the determined temperature and pressure being applied to the vessel "V," rupturing (e.g., via micro-tears) of the vessel "V" from steam generated within the vessel "V" during the sealing process. The temperature and/or pressure applied to the vessel "V" may be reduced upon determining that the pressure within the vessel "V" is approaching a threshold amount known to rupture the vessel "V." The temperature and pressure applied to the vessel "V" may be increased upon determining that all water has been vaporized from the vessel "V."

The system 1000 may be configured to provide a visual or auditory warning when the jaws 1202, 1204 reach a temperature known to cause damage to adjacent and delicate tissue structures. In aspects, pressure sensors (not explicitly shown) in the jaws 1202, 1204 may be configured to send to the display 1006 for display the amount of pressure being applied on the vessel "V" or other tissue being grasped by the jaws 1202, 1204. A visual or auditory warning may be provided upon the pressure applied to the tissue exceeding a threshold pressure known to damage tissue.

The flow diagram described above includes various blocks described in an ordered sequence. However, those skilled in the art will appreciate that one or more blocks of the flow diagram may be performed in a different order, repeated, and/or omitted without departing from the scope of the disclosure. The above description of the flow diagram refers to various actions or tasks performed by the robotic surgical system 1000, but those skilled in the art will appreciate that the robotic surgical system 1000 is exemplary. In various embodiments, the disclosed operations can be performed by a clinician or another component, device, or system. In various embodiments, the robotic surgical system 1000 or other component/device performs the actions or tasks via one or more software applications executing on the processor. In various embodiments, at least some of the operations can be implemented by firmware, programmable logic devices, and/or hardware circuitry. Other implementations are contemplated to be within the scope of the disclosure.

It should be understood that the foregoing description is only illustrative of the disclosure. Various alternatives and modifications can be devised by those skilled in the art without departing from the disclosure. Accordingly, the disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A method of performing a tissue seal utilizing a robotic surgical system, comprising:
    grasping tissue between a pair of jaws of an electrosurgical instrument coupled to a robotic surgical system;
    displaying on a display of the robotic surgical system a virtual image of the tissue and a property of the virtual image of the tissue;
    emitting electrosurgical energy from the pair of jaws into the grasped tissue, thereby changing at least one of a temperature of the grasped tissue or a perfusion of the grasped tissue;
    stopping emission of the electrosurgical energy after emitting the electrosurgical energy for a predetermined amount of time corresponding to about a 5 percent completion of a seal of the tissue to about a 20 percent completion of the seal of the tissue; and
    displaying on the display a visual representation of at least one of the change of the temperature of the grasped tissue or the change of the perfusion of the grasped tissue as the electrosurgical energy is emitted from the pair of jaws into the grasped tissue by changing the displayed property of the virtual image of the tissue.

2. The method according to claim 1, further comprising:
    stopping emission of the electrosurgical energy after emitting the electrosurgical energy for a predetermined amount of time; and
    determining a status of the tissue.

3. The method according to claim 2, further comprising restarting emission of the electrosurgical energy into the tissue after the status of the tissue is determined.

4. The method according to claim 3, further comprising adjusting a level of the electrosurgical energy based on the determined status of the tissue.

5. The method according to claim 4, further comprising adjusting a grasping pressure applied to the tissue by the pair of jaws based on the determined status of the tissue.

6. The method according to claim 2, wherein the status of the tissue is determined based on at least one of the temperature of the grasped tissue or the perfusion of the grasped tissue.

7. The method according to claim 2, wherein the status of the tissue is determined based on a temperature of each of a plurality of sections of the tissue.

8. The method according to claim 2, wherein the predetermined amount of time corresponds to about a 5 percent completion of a seal of the tissue to about a 20 percent completion of the seal of the tissue.

9. The method according to claim 1, further comprising displaying on the display a visual representation of a progress of a seal of the tissue as the electrosurgical energy is emitted from the pair of jaws into the grasped tissue, wherein the visual representation of the progress of the seal includes a number representing a percentage of a completed seal of the tissue.

10. The method according to claim 1, further comprising displaying on the display a visual representation of a level of electrosurgical energy being emitted by the pair of jaws into the grasped tissue.

11. The method according to claim 1, further comprising displaying on the display a temperature of the pair of jaws.

12. The method according to claim 1, further comprising:
    determining a size of the grasped tissue; and
    displaying on the display a visual representation of the determined size of the grasped tissue.

13. A method of performing a tissue seal utilizing a robotic surgical system, comprising:
    displaying on a display of the robotic surgical system a visual representation of tissue grasped between a pair of jaws of an electrosurgical instrument coupled to a robotic surgical system;

emitting electrosurgical energy from the pair of jaws into the grasped tissue, thereby changing at least one of a temperature of the grasped tissue or a perfusion of the grasped tissue;

stopping emission of the electrosurgical energy after emitting the electrosurgical energy for a predetermined amount of time corresponding to about a 5 percent completion of a seal of the tissue to about a 20 percent completion of the seal of the tissue; and displaying on the display a visual representation of at least one of the change of the temperature of the grasped tissue or the change of the perfusion of the grasped tissue as the electrosurgical energy is emitted from the pair of jaws into the grasped tissue.

14. The method according to claim 13, further comprising determining a status of the grasped tissue while the emission of the electrosurgical energy is stopped.

15. The method according to claim 14, further comprising restarting emission of the electrosurgical energy into the grasped tissue after the status of the tissue is determined.

16. The method according to claim 13, wherein displaying on the display the visual representation of at least one of the change of the temperature of the grasped tissue or the change of the perfusion of the grasped tissue includes changing a displayed property of the visual representation of the tissue.

17. The method according to claim 16, wherein the displayed property of the visual representation of the tissue is at least one of a color, a pattern, or a shading of the visual representation of the tissue.

18. A method of treating tissue utilizing a robotic surgical system, comprising:

displaying on a display of the robotic surgical system a visual representation of tissue;

emitting electrosurgical energy into the tissue, thereby changing at least one of a temperature of the tissue or a perfusion of the tissue;

stopping emission of the electrosurgical energy after emitting the electrosurgical energy for a predetermined amount of time corresponding to about a 5 percent completion of treatment of the tissue to about a 20 percent completion of the treatment of the tissue; and displaying on the display a visual representation of at least one of the change of the temperature of the tissue or the change of the perfusion of the tissue.

19. The method according to claim 18, further comprising determining a status of the tissue while the emission of the electrosurgical energy is stopped.

20. The method according to claim 18, further comprising causing a pair of jaw members of an electrosurgical instrument to grasp the tissue.

* * * * *